(12) United States Patent
Rossano et al.

(10) Patent No.: US 9,914,513 B2
(45) Date of Patent: Mar. 13, 2018

(54) TRANSFORMER IN-SITU INSPECTION VEHICLE WITH A CAGE HULL

(71) Applicant: ABB SCHWEIZ AG, Baden (CH)

(72) Inventors: Gregory F. Rossano, Enfield, CT (US); William Eakins, Bloomfield, CT (US); Daniel T. Lasko, Bloomfield, CT (US); Thomas A. Fuhlbrigge, Ellington, CT (US); Andrew M. Salm, West Hartford, CT (US); George Zhang, Windsor, CT (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 14/535,417

(22) Filed: Nov. 7, 2014

(65) Prior Publication Data

US 2016/0129979 A1    May 12, 2016

(51) Int. Cl.
| | |
|---|---|
| *B63G 8/00* | (2006.01) |
| *G21C 17/013* | (2006.01) |
| *B63G 8/04* | (2006.01) |
| *G01D 11/24* | (2006.01) |
| *G01N 21/88* | (2006.01) |
| *G01R 31/02* | (2006.01) |

(Continued)

(52) U.S. Cl.
CPC ............. *B63G 8/001* (2013.01); *B63G 8/04* (2013.01); *G01D 11/24* (2013.01); *G01N 21/88* (2013.01); *G01R 31/027* (2013.01); *G21C 17/013* (2013.01); *B63G 8/08* (2013.01); *B63G 8/22* (2013.01); *B63G 2008/002* (2013.01); *E21B 2023/008* (2013.01); *G01M 3/38* (2013.01); *G01N 2021/0112* (2013.01); *H01F 27/12* (2013.01)

(58) Field of Classification Search
CPC ............. B63G 8/001; B63G 2008/002; B63G 2008/004; B63G 2008/005; B63G 2008/007; G01M 3/005; A63H 23/06
See application file for complete search history.

(56) References Cited

U.S. PATENT DOCUMENTS

| | | | |
|---|---|---|---|
| 3,694,094 A | 9/1972 | Low et al. | ...................... 356/241 |
| 3,766,582 A * | 10/1973 | Lloyd | .................. B63B 35/4406 |
| | | | 405/202 |

(Continued)

FOREIGN PATENT DOCUMENTS

| | | |
|---|---|---|
| EP | 2762279 A1 | 8/2014 |
| JP | 6133371 A | 5/1994 |

(Continued)

OTHER PUBLICATIONS

International Search Report dated May 19, 2014 in corresponding application No. PCT/US2014/012920.

(Continued)

*Primary Examiner* — Andrew Polay
(74) *Attorney, Agent, or Firm* — Taft Stettinius & Hollister LLP

(57) ABSTRACT

An inspection device for use in a fluid container includes at least one thrust device, at least one ballast device and a cage which carries the at least one thrust device and the at least one ballast device. The cage includes at least two bars. Each bar provides an opening, the openings forming a cage cavity to carry the at least one thrust device and the at least one ballast device.

18 Claims, 6 Drawing Sheets

(51) Int. Cl.
  *G01M 3/38*      (2006.01)
  *E21B 23/00*     (2006.01)
  *B63G 8/08*      (2006.01)
  *G01N 21/01*     (2006.01)
  *B63G 8/22*      (2006.01)
  *H01F 27/12*     (2006.01)

(56) References Cited

U.S. PATENT DOCUMENTS

| | | | |
|---|---|---|---|
| 5,703,377 A | 12/1997 | Ainsworth et al. | 250/559.45 |
| 6,257,502 B1 * | 7/2001 | Hanish | B05B 1/14 |
| | | | 239/290 |
| 7,025,014 B1 * | 4/2006 | Forgach | B63B 21/66 |
| | | | 114/244 |
| 7,131,344 B2 | 11/2006 | Tarumi | 73/865.8 |
| 7,940,297 B2 | 5/2011 | Penza et al. | 348/84 |
| 9,168,990 B2 * | 10/2015 | Webb | G01C 13/00 |
| 2010/0180672 A1 | 7/2010 | Zollinger | 73/61.63 |
| 2012/0257704 A1 | 10/2012 | Asada et al. | 376/249 |
| 2013/0033594 A1 | 2/2013 | Smith et al. | 348/83 |
| 2014/0360420 A1 * | 12/2014 | Scott | B63G 8/08 |
| | | | 114/337 |

FOREIGN PATENT DOCUMENTS

| | | | | |
|---|---|---|---|---|
| JP | 8240689 A | 9/1996 | | |
| JP | 9159614 A | 6/1997 | | |
| JP | 11188327 A | 7/1999 | | |
| JP | 2000046742 A | 2/2000 | | C12C 13/00 |
| JP | 2008261807 A | 10/2008 | | G21C 17/003 |
| JP | 2009109353 A | 5/2009 | | G01N 21/84 |
| WO | WO 2006/078873 A2 | 7/2006 | | |
| WO | WO 2009/029216 A1 | 3/2009 | | A61B 18/18 |
| WO | 2010/040171 A1 | 4/2010 | | |
| WO | 2013/152974 A1 | 10/2013 | | |

OTHER PUBLICATIONS

Written Opinion dated May 19, 2014 in corresponding application No. PCT/US2014/012920.
Patent Cooperation Treaty International Search Report dated Feb. 4, 2016 cited in counterpart PCT/US2015/058718 (4 pages).
Patent Cooperation Treaty Written Opinion of the International Searching Authority dated Feb. 4, 2016 cited in counterpart PCT/US2015/058718 (4 pages).

* cited by examiner

TRANSFORMER IN-SITU INSPECTION VEHICLE WITH A CAGE HULL

TECHNICAL FIELD

Generally, the present invention is directed to transformer inspection systems. Specifically, the present invention is directed to a remotely controlled inspection device inserted into a liquid-filled transformer. More particularly, the present invention is directed to an inspection device which has a cage hull with openings therethrough that reduces turbulence as the device moves in the oil of a transformer.

BACKGROUND ART

Liquid-filled power transformers are one of the key components in power transformation and distribution. The liquid is used to cool the internal components of the transformer during its operation. As is well understood, the large liquid-filled power transformers are extremely heavy and difficult to transport and replace. They have a limited life span and necessary maintenance and repair are needed periodically.

While non-invasive techniques are now used to identify potential problems that the transformer may have; the common way to directly observe the windings, cables, supports and connectors inside a transformer tank is to drain the liquid from the transformer tank and send in a person through a manhole or open the transformer tank by cutting a top plate from the tank. Therefore, there is a need in the art for a device that easily moves in a controlled matter for in-situ inspection of a transformer.

SUMMARY OF THE INVENTION

In light of the foregoing, it is a first aspect of the present invention to provide a transformer in-situ inspection vehicle with a cage hull.

Another aspect of the present invention is to provide an inspection device for use in a fluid container, comprising at least one thrust device, at least one ballast device, a cage which carries the at least one thrust device and the at least one ballast device, the cage comprising at least two bars, each bar providing an opening wherein the openings form a cage cavity to carry the at least one thrust device and the at least one ballast device.

Yet another aspect of the present invention is to provide an inspection device for use in a fluid comprising at least one component, a cage which internally carries the at least one component, the cage having a plurality of bars with openings therebetween which allow fluid to flow therethrough and around the at least one component.

BRIEF DESCRIPTION OF THE DRAWINGS

These and other features and advantages of the present invention will become better understood with regard to the following description, appended claims, and accompanying drawings. The figures may or may not be drawn to scale and proportions of certain parts may be exaggerated for convenience of illustration:

DETAILED DESCRIPTION OF THE INVENTON

Figure 1:
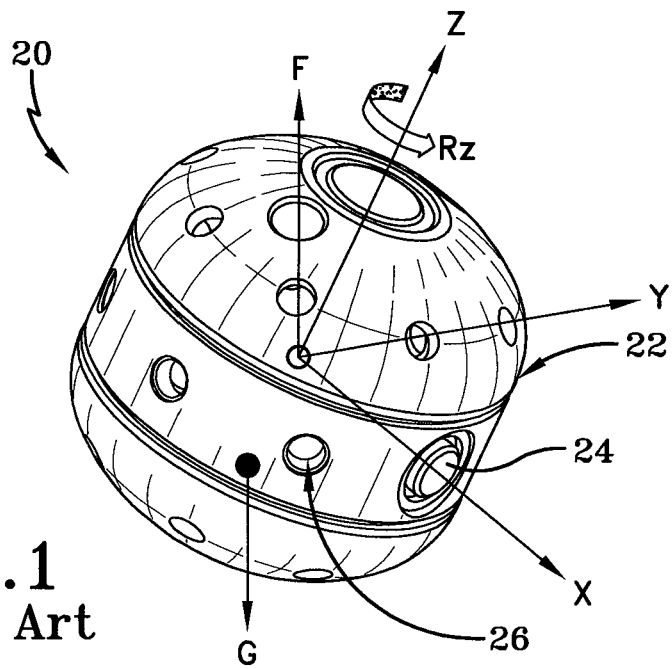
FIG. 1 is a schematic drawing of a prior art inspection device.
Figure 2:
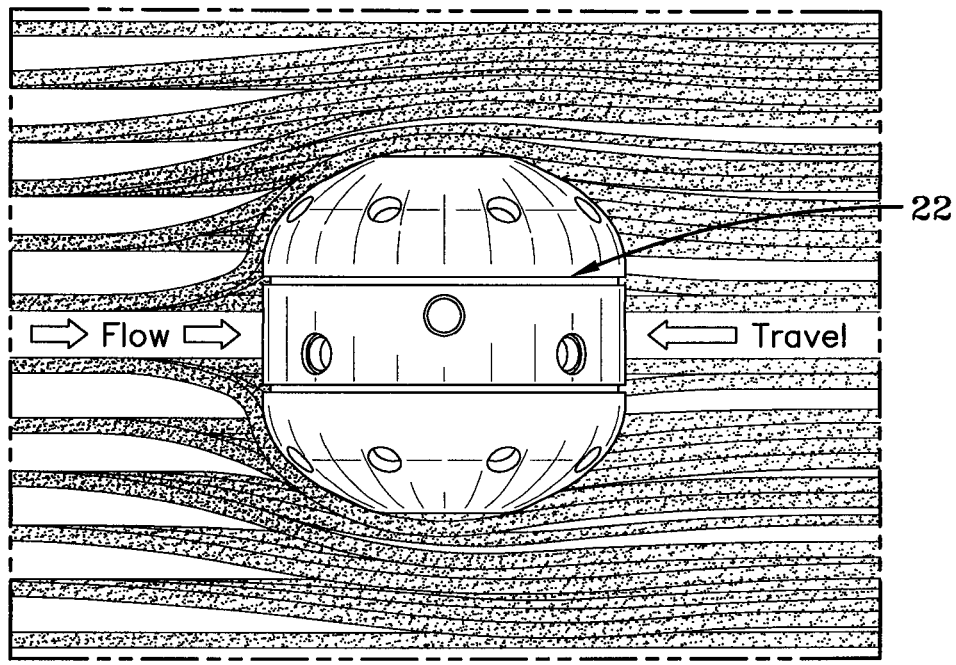
FIG. 2 is a schematic flow simulation of the prior art inspection device showing the turbulence generated by such a device.

Referring now to the drawings and in particular to FIGS. 1 and 2 it can be seen that a prior art inspection device is designated generally by the numeral 20. The device 20 is utilized for inspection of a transformer which contains high-voltage electrical components immersed in a cooling fluid such as oil. The transformer is not shown, but skilled artisans will appreciate that the inspection occurs only when the transformer is off-line or not in use. As will be appreciated by skilled artisans, the transformer utilizes cooling fluid so as to maintain and disperse heat generated by the internal components during operation of the transformer. Although the prior art inspection device and the present embodiment to be discussed is directed to systems for inspecting electrical transformers, it will be appreciated that the teachings disclosed herein may be applicable to any inspection device used in a relatively large volume sealed container, such as a tank, which maintains a fluid. The transformer is maintained in a sealed configuration so as to prevent contaminants or other matter from entering. The tank will be provided with at least one opening to allow for the filling and/or draining of the cooling fluid. So as to reduce the downtime of emptying a transformer of the cooling fluid and conducting a manual visual inspection, the use of the inspection device 20 allows for a remote inspection without having to drain the cooling fluid from the tank.

The prior art inspection device 20 is insertable into the transformer or sealed container and is movable utilizing an un-tethered, wireless remote control. The inspection device 20 provides for a housing 22 which totally encloses a number of sensors and control electronics 24 such as a camera or the like. One purpose of the housing is to protect the device's internal components. The housing 22 does provide for openings 26 that are utilized by thrusters which control positioning of the housing 22 within the transformer. As such, a technician may control positioning of the inspection device within the transformer so as to inspect any of the components contained within the transformer. However, as shown in FIG. 2, it can be seen that the housing 22 generates significant turbulence when moving within the transformer. This turbulence causes difficulty in moving the inspection device within the transformer, thus hampering its usefulness.

Figure 3:
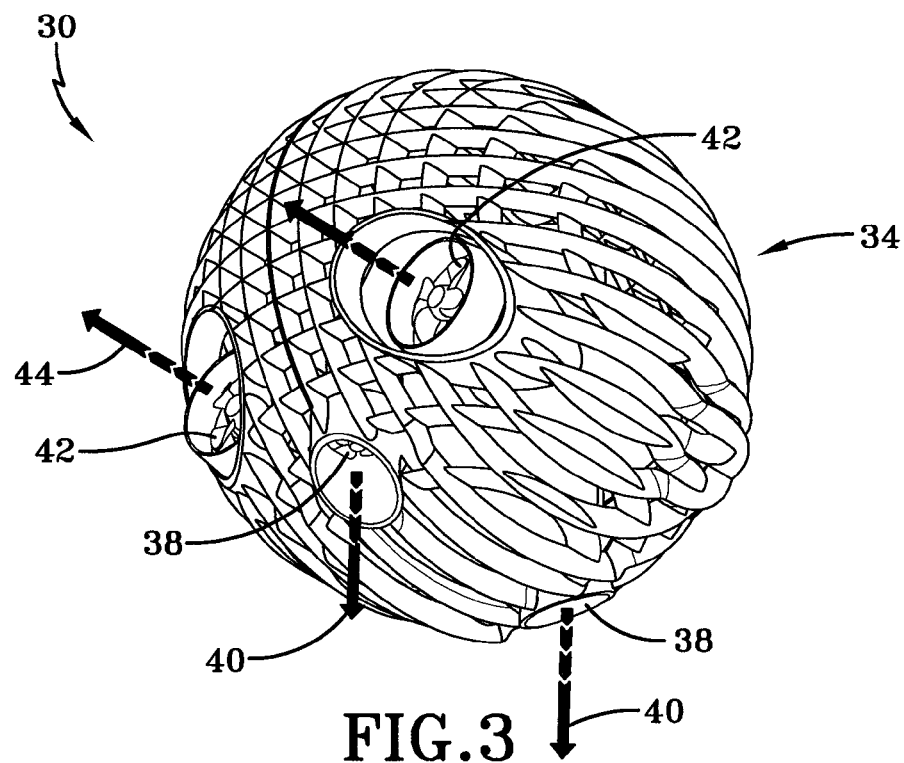
FIG. 3 is a rear perspective view of an inspection device made in accordance with the concepts of the present invention.
Figure 4:
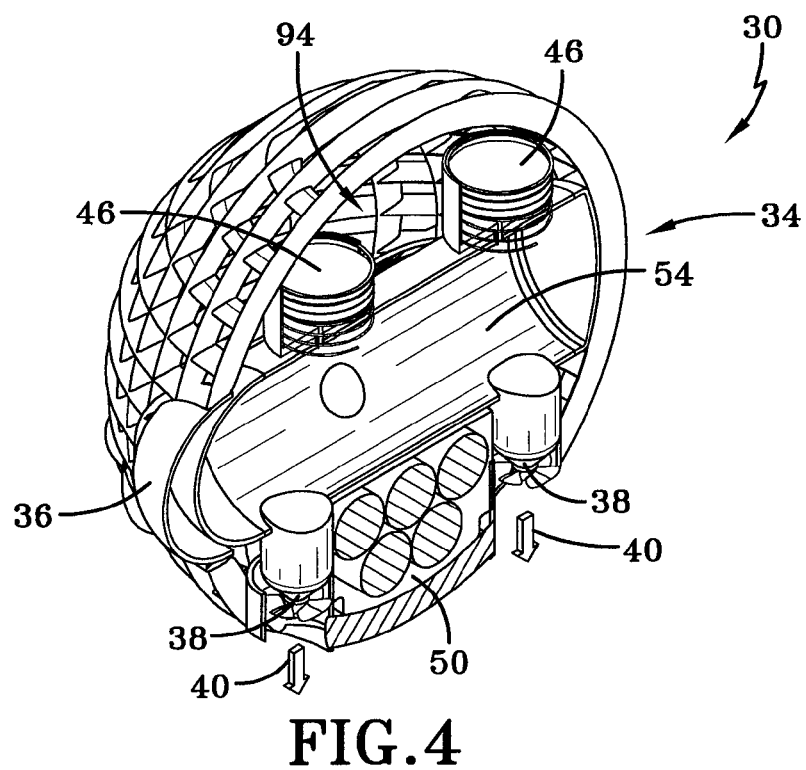
FIG. 4 is a cross-sectional view of the inspection device made in accordance with concepts of the present invention.
Figure 5:
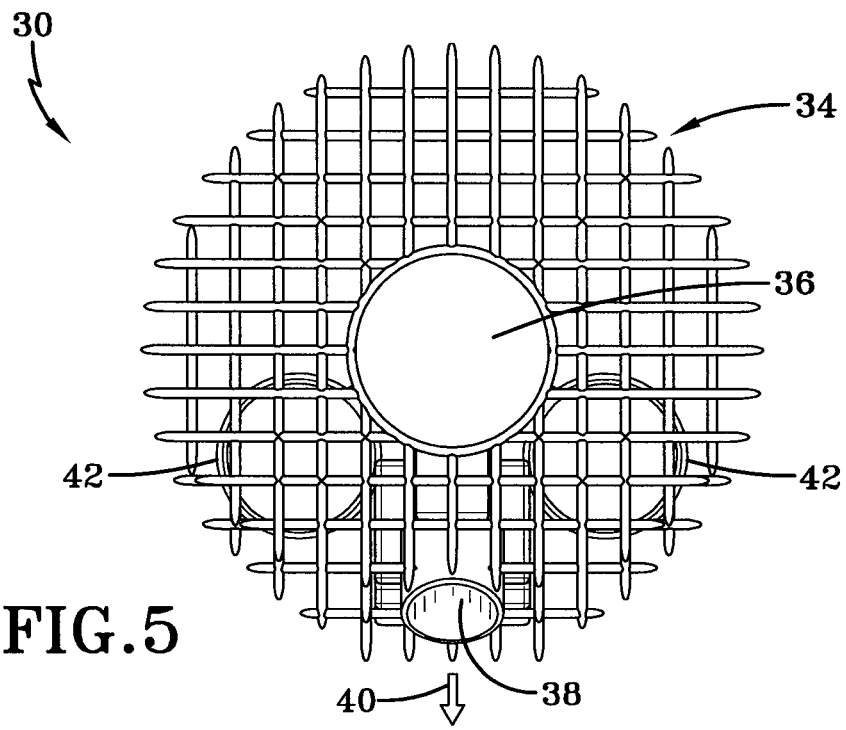
FIG. 5 is a front elevational view of the inspection device made in accordance with the concepts of the present invention.
Figure 6:
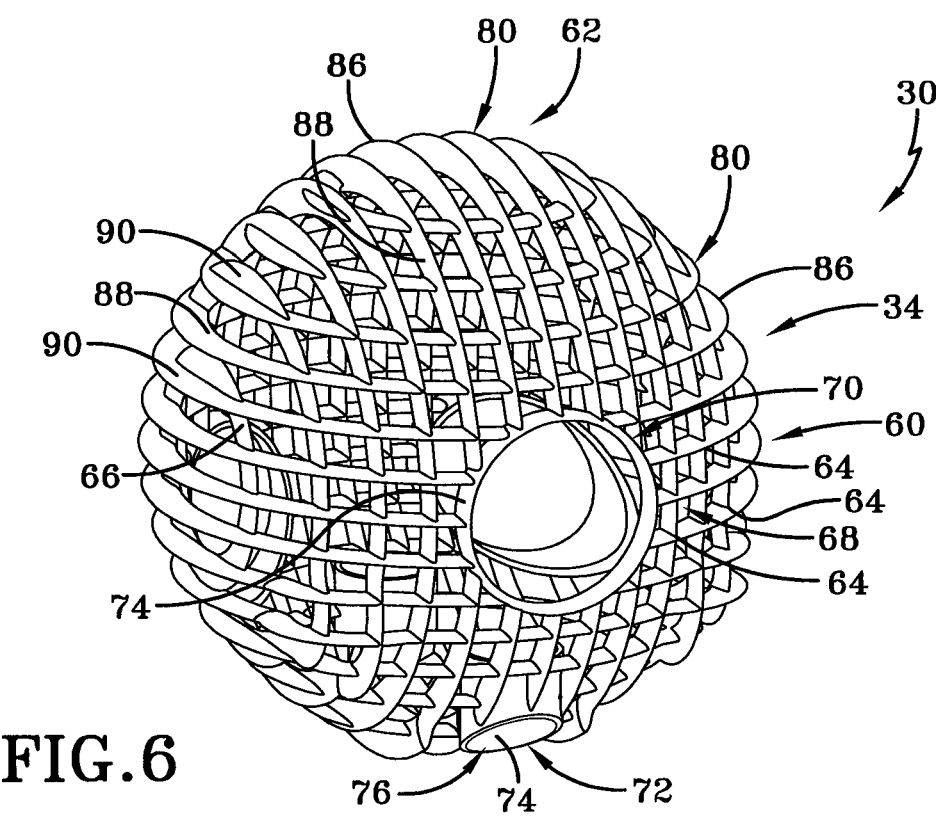
FIG. 6 is a perspective view of a cage hull utilized by the inspection device which substantially encloses the internal components of the device in accordance with the concepts of the present invention.

Referring now to FIGS. 3-5 it can be seen that an inspection device with improved movement control properties is designated generally by the numeral 30. The device 30 includes a cage hull 34 which holds the internal components of the device which are utilized to facilitate operation of the device. The cage hull 34, which may also be considered a grid-style hull, may include at least one sensor 36 such as a camera which may remotely transmit pictures or video to a technician for evaluation. The sensors may also include, but are not limited to, temperature sensors, viscosity sensors to detect specific materials and the like. Maintained by the cage hull 34 is at least one vertical thruster 38 which when actuated generates a thrust vector 40 so as to move the device 30 in a generally vertical direction. As best seen in FIGS. 3 and 4, two vertical thrusters 38 may be provided. The device 30 may also provide for at least one horizontal thruster 42 which generates a thrust vector 44. As best seen in FIGS. 3 and 5, two horizontal thrusters 42 may be provided.

Ballast devices 46 may be provided within the cage hull 34 so as to control the equilibrium positioning of the device. In other words, control of the ballast allows the device's natural buoyancy to be controlled as deemed appropriate by the technician. In the present embodiment, the at least one ballast device 46 selectively allows oil from within the tank to be received. This reduces the volume of the device which can then be used to lower the device in the tank. This reduction of the volume provides desired buoyancy balance to the device 30 while it moves within the tank. If needed, the ballast device(s) can be controlled to release the retained oil to increase the volume of the device and permit the device to rise without use of the thrusters.

A battery compartment 50 may be maintained within the device 30 and is utilized to carry the batteries that power the various components within the device. These powered components may include the various sensors, the ballast devices, the thrusters and in particular the motors or pumps utilized to operate the thrusters. At least one light may be provided so as to illuminate the immediate area of the device. An electronics bay 54 may also be provided in the device so as to contain the electronics and control devices utilized to operate the various sensors, thrusters, lights and other components of the device. The light, and the electronics and control devices, may be powered by the batteries. Skilled artisans will appreciate that selective control of the thrusters in either the vertical and/or horizontal direction allow for movement of the device in six degrees of freedom within the transformer.

Referring now to FIGS. 6-10 it can be seen that the cage hull 34 is constructed from at least one bar 60 oriented in a first orientation and at least one second bar 62 oriented in a second orientation. At a minimum, the bar 60 and the bar 62 intersect with one another at an intersection point 64. The bars 60 and 62 form the cage hull 34 such that the internal components are internally maintained within the inner periphery of the bars 60 and 62. In one embodiment a plurality of bars 60 may be provided in the first orientation and a plurality of bars 62 may be provided in the second orientation. In other embodiments the bars 60 are equaldistantly spaced apart from one another or they may be spaced at predetermined intervals. The bars 62 may be likewise spaced equidistantly or at predetermined intervals. In one embodiment the bars 60 are provided in parallel configurations and the bars 64 are likewise provided in parallel configurations. In the embodiment shown, the bars 60 and 62 are maintained substantially perpendicular with one another and equidistantly spaced, however, in other embodiments the bars 60 and 62 may be configured at any other angular orientation. Wherever adjacent bars 60 and adjacent bars 62 intersect with one another, they form a grid 66 wherein a cage opening 68 is provided between the interconnected bars. The number and orientation of the bars 60 and 62 will control the number of grids and the corresponding number of cage openings 68 provided by the hull 34. Although two orientations of the bars 60 and 62 are shown, skilled artisans will appreciate that the bars could be spaced and/or positioned in three or more orientations.

The bars 60 and 62 may provide at least one sensor port 70 which provides structural support to carry the sensor 36 or the like by the hull 34 and in such a manner that the bars do not block or interfere with the operation of the sensor. The hull 34 may also provide for at least one thruster port 72 which surrounds the output of the thruster mechanisms such as a propeller or the like. The port 70 and the port 72 may include a port wall 74 which effectively terminates each bar 60 or 62 that intersects with the wall 74. As a result, the wall 74 defines and forms a port opening 76 such that the bars 60 or 62 do not extend into the opening 76.

The bars 60/62, in any of the embodiments disclosed, may have a cross section that could be circular, much like a wire; a plank-shape, a slat shape or whatever appropriate cross-sectional shape that could be implemented. As is evident in FIGS. 7A and 7B, each bar 60/62 may have a circular-shaped body 80 and a body opening 82 extending therethrough. Each bar, as seen in FIGS. 6 and 8-10, and in particular each circular body 80, may be of a different outer diameter and wherein the body opening 82 may have a correspondingly different inner diameter. By arranging the different diameter sizes of the bars 60/62, a spherical shape of the hull 30 may be obtained. Of course various combinations of the outer diameter and/or shape of the bars 60/62 may be implemented to obtain other shapes for the hull or to accommodate the internal components. It is believed that a spherical shape of the hull provides for the best maneuverability characteristics of the submersible device within the transformer or other container. However, skilled or artisans will appreciate that other shapes, such as elliptical, square, triangular or any combination of shapes, may be used in other embodiments. And it will be appreciated that the device may selectively control operation of the vertical thrusters and horizontal thrusters to propel the device as needed. It will further be appreciated that the at least one ballast device that is maintained within the hull may be utilized to control positioning of the device as needed.

Figure 7A:
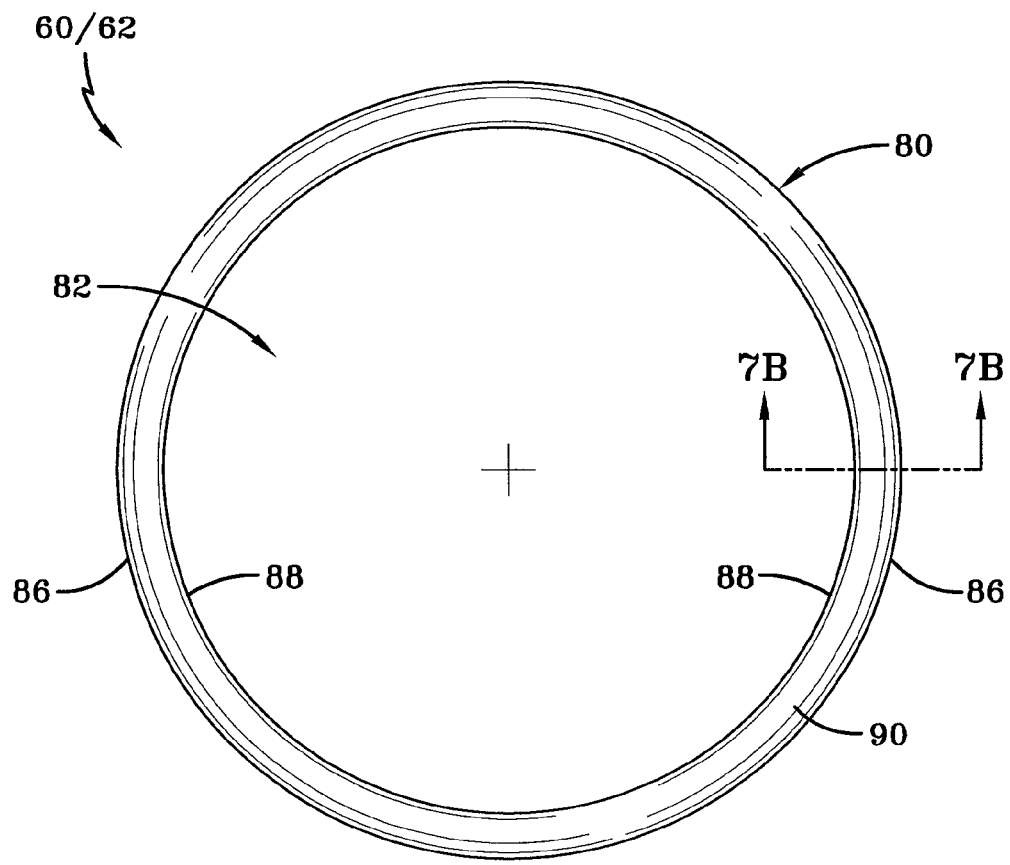
FIG. 7A is a top plan view of an exemplary bar used with a plurality of other bars to form the cage hull according to the concepts of the present invention.
Figure 7B:
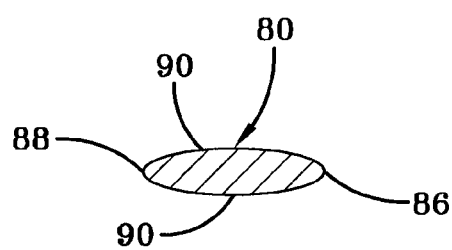
FIG. 7B is a cross-sectional view taken along line 7B-7B of FIG. 7A of the exemplary bar.
Figure 8:
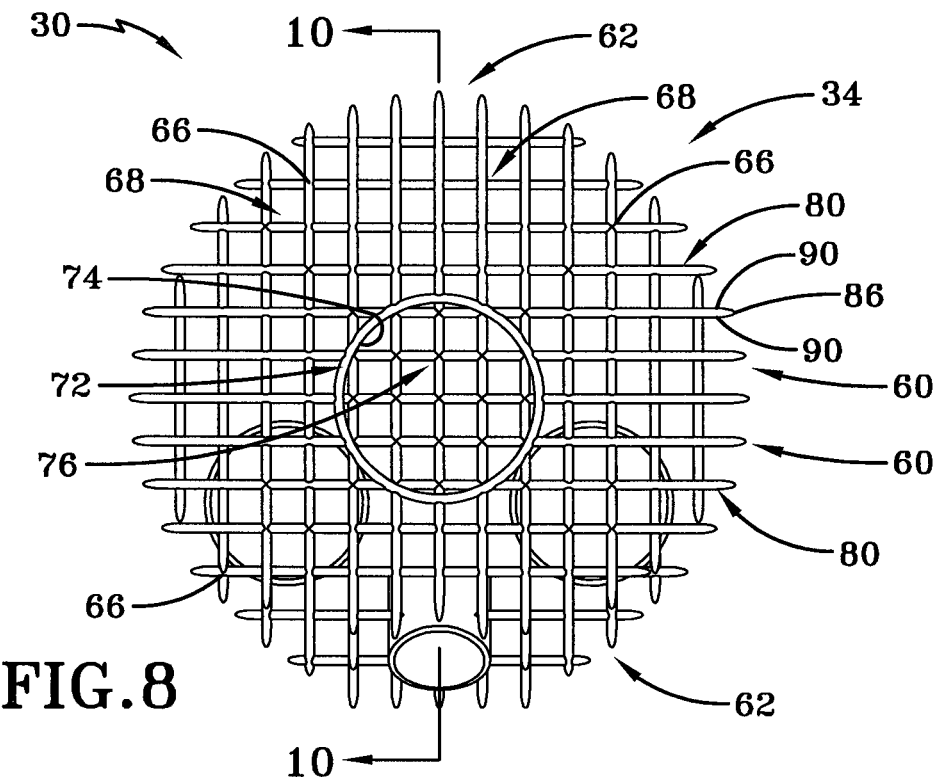
FIG. 8 is a front elevational view of the cage hull with the internal components removed according to the concepts of the present invention.
Figure 9:
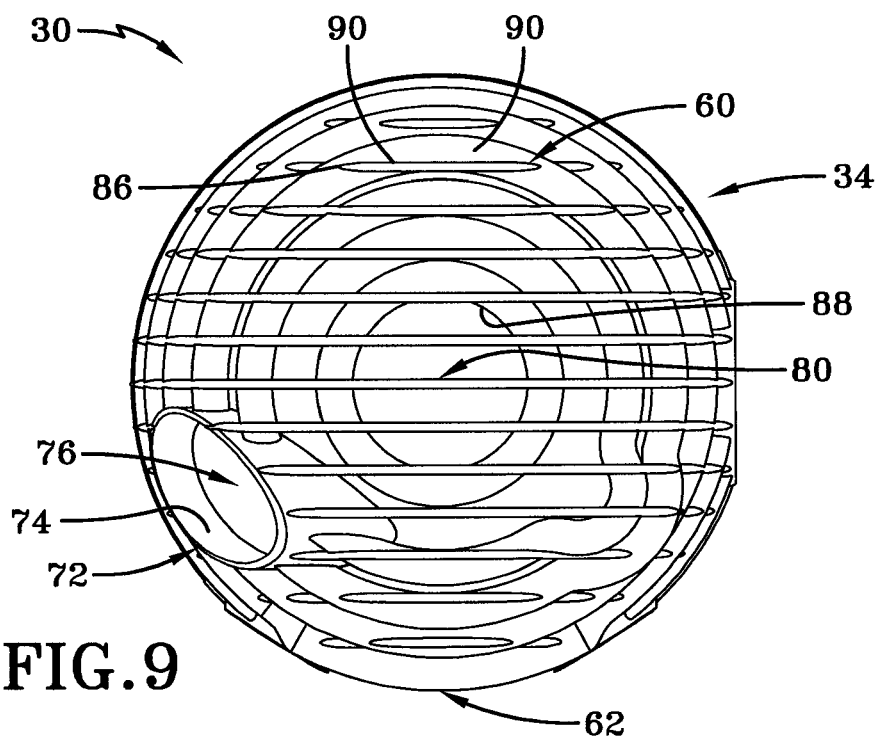
FIG. 9 is a side elevational view of the cage hull with the internal components removed according to the concepts of the present invention.

In one embodiment, each circular body 80, as seen in FIG. 7B, may have a cross section that is substantially of a slat shape. As such, the body 80 has a leading edge 86 that faces outwardly from the hull and a trailing edge 88 that faces inwardly. Connecting the leading edge 86 and the trailing edge 88 are opposed bar surfaces 90. In one embodiment the bar surfaces 90 may be planar or flat and in another embodiment the bar surfaces may be curved. In particular, the curved bar surfaces 90 may be convex shaped. When the bars are provided in a slat shape, it will be appreciated that the slat shape provides more control and stability while propelling the in-situ inspection device in a fluid. As a result, the bars act as small fins or rudders that reduce the turbulence and allow the inspection device to stay on a predetermined course as controlled by the technician. The shaped configuration of the leading edge, the trailing edge and the surfaces 90 may be adjusted so as to improve the maneuverability of the device. Moreover, selected bars 60/62 of the circular body 80 may have their particular shapes or cross-section configuration adjusted as deemed appropriate. In other words, the smaller diameter body(s) may have one particular cross-sectional shape, while the inner or larger diameter body(s) may have another cross-sectional shape. The cross-sectional shape of each bar may be used with the force generated by each thruster 38 and 42 and their corresponding thrust vectors 40 and 44. The orientational alignment of the bars and in particular the leading edges 86, the trailing edges 88 and the opposed bar surfaces may be oriented and aligned with the thrust vector(s). In other words, the orientational alignment of the shape of bars minimizes the area of the cross section of the cage hull. This reduces the drag forces in relation to the thrust vector direction.

Figure 10:
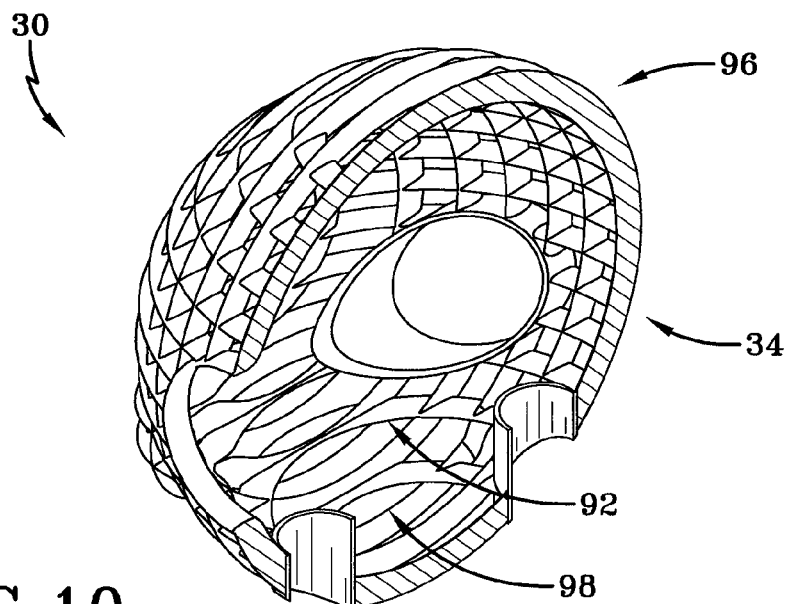
FIG. 10 is a cross-sectional elevational view of the cage hull with the internal components removed according to the concepts of the present invention.

As best seen in FIG. 10, the inner diameter of the bars 60/62 form a cage cavity 92 that is formed by the trailing edges 88 of all the bars provided. The cage cavity 92 is the area in which the internal components are carried and maintained. In some embodiments selected portions of the internal components may extend beyond the leading edges or may be maintained flush with the leading edges of the bars 60/62. In order to prevent entanglement of the device it is believed that extension of the internal components beyond the spherical shape or envelope shape of the hull should be kept to a minimum. Any space within the cage cavity 92 not filled by the internal components forms cage voids designated by the numeral 94 (see FIG. 4). The leading edges 86 collectively form a cage exterior surface 96 while the collective trailing edges 88 of the bars 60/62 form a cage interior surface 98 which define the cage cavity 92.

Figure 11:
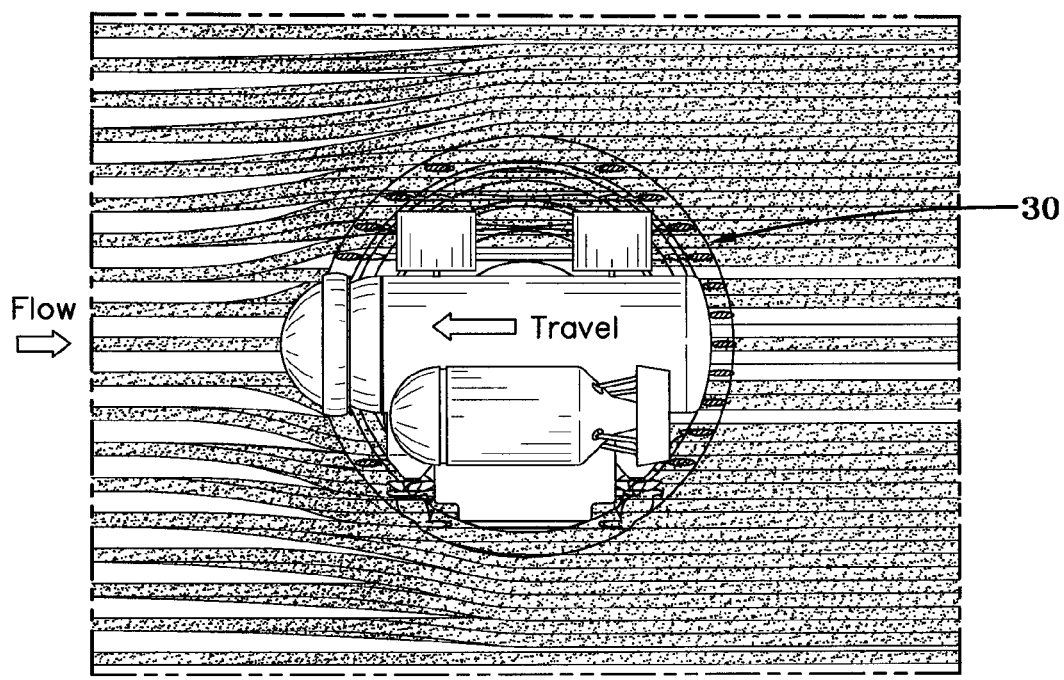
FIG. 11 is a schematic flow simulation of the inspection device showing the reduced turbulence generated by such a device.

In operation, as the thrusters are actuated and/or the at least one ballast device controlled, the device 30 moves through the fluid contained in the transformer or other container. As best seen in FIG. 11, the flow of the device and the spacing provided between the bars 60 and 62 allow the fluid to at least partially flow through the device. This significantly reduces the turbulence generated by the moving device so as to maintain the stability and maneuverability of the device as desired. Moreover, the slat configuration provided in the disclosed embodiment allows the slats to function like a rudder device so as to maintain forward and reverse directions of the device as it moves throughout the transformer. Such a hull shape design also increases the lateral resistance in the non-thrusting direction, which will result in the same effect as a rudder. In other words, the opposed bar surfaces 90, whatever shape they may be, effectively reduce the movement of the hull in a direction normal to the bar surfaces.

The advantages of the present construction are readily apparent to those skilled in the art. The openings allow for fluid to flow through the device so as to minimize turbulence that would otherwise be caused. Such a configuration also allows for the device to move more quickly as less resistance is encountered in the direction of movement.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. An inspection device for use in a fluid container, comprising:
   at least one thruster;
   at least one ballast device;
   a cage which carries said at least one thruster and said at least one ballast device, said cage comprising a plurality of bars, each of said bars arcuately formed around an opening wherein said opening forms a cage cavity to carry said at least one thruster and said at least one ballast device; and wherein the plurality of bars includes:
      a first set of at least two bars formed around the opening and oriented in a first direction in substantially parallel planes to one another; and
      a second set of at least two bars formed around the opening and oriented in a second direction in substantially parallel planes to one another.

2. The device according to claim 1, wherein said at least one thruster and said ballast device are carried within said cage cavity.

3. The device according to claim 1, wherein said first and second directions are substantially perpendicular with one another.

4. The device according to claim 1, wherein said first and second set of at least two bars intersect with one another at intersection points, wherein said intersection points and adjacent bars form the cage opening.

5. The device according to claim 4, wherein said cage opening is contiguous with said cage cavity to allow fluid in the fluid container to flow through said cage when said at least one thruster is activated.

6. The device according to claim 4, wherein each said bar is a slat that has a leading edge opposite a trailing edge, wherein said leading edges form a cage exterior.

7. The device according to claim 6, wherein each said slat has opposed surfaces connecting said leading edge to said trailing edge.

8. The device according to claim 7, wherein said at least one thruster has a thrust vector wherein said opposed surfaces are oriented with said thrust vector.

9. The device according to claim 1, wherein each said bar is a slat that has a leading edge opposite a trailing edge, wherein said leading edge and said trailing edge are connected by opposed surfaces which are oriented in a same direction as a thrust vector generated by said at least one thruster.

10. The device according to claim 1, wherein said first set of at least two bars and said second set of at least two bars intersect with each other at an intersection point.

11. The device according to claim 1, wherein said cage is substantially spherical.

12. An inspection device for use in a fluid comprising:
   at least one component included from the following: a sensor, control electronics and/or a camera;
   a cage having a cavity which internally carries said at least one component, said cage having a plurality of bars with openings therebetween, the plurality of bars formed in an arcuate shape to define the cage cavity internal thereto, wherein at least two of the plurality of bars are oriented in parallel planes relative to one another, and wherein the openings allow fluid to flow therethrough and around said at least one component;
   at least one thruster for propelling the cage through the water;
   a battery compartment structured to carry a power source useful to provide power to the at least one thruster;

wherein said plurality of bars comprise a first bar oriented in a first direction, a second bar oriented in a second direction, and wherein said first bar is connected to said second bar at an intersection point; and wherein each of said first bar and second bar have a circular body.

13. The device according to claim 12, wherein a portion of said plurality of bars are oriented in a first direction, the device further comprising:

at least one interconnecting bar to connect adjacent bars oriented in said first direction.

14. The device according to claim 12, wherein each of said plurality of bars have a body opening therethrough.

15. The device according to claim 14, wherein at least one of said plurality of bars is a slat having a leading edge opposite a trailing edge.

16. An inspection device for use in a fluid comprising:

at least one component included from the following: a sensor, control electronics and/or a camera;

a cage having a cavity which internally carries said at least one component, said cage having a plurality of bars with openings therebetween, the plurality of bars formed in an arcuate shape to define the cage cavity internal thereto, wherein at least two of the plurality of bars are oriented in parallel planes relative to one another, and wherein the openings allow fluid to flow therethrough and around said at least one component;

wherein each of said plurality of bars have a circular body which has a body opening therethrough, and wherein at least two of said circular bodies have a different outer diameter;

wherein at least one of said plurality of bars is a slat having a leading edge opposite a trailing edge; and wherein said at least one component further includes a thruster which generates a thrust vector which is aligned in a same orientation as said leading and trailing edges.

17. The device according to claim 15, wherein said at least one component further includes a thruster which generates a thrust vector which is aligned in a same orientation as said leading and trailing edges.

18. The device according to claim 12, wherein each of said plurality of bars have a circular body, and wherein at least two of said circular bodies have a different outer diameter.

* * * * *